United States Patent
Matsumoto

(10) Patent No.: US 11,185,651 B2
(45) Date of Patent: Nov. 30, 2021

(54) CONGESTIVE HEART FAILURE THERAPY DEVICE WITH POSITIVE PRESSURE ADJUSTMENT

(71) Applicant: Teijin Pharma Limited, Tokyo (JP)

(72) Inventor: Sadayoshi Matsumoto, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 346 days.

(21) Appl. No.: 15/571,714

(22) PCT Filed: Jun. 28, 2016

(86) PCT No.: PCT/JP2016/069181
§ 371 (c)(1),
(2) Date: Nov. 3, 2017

(87) PCT Pub. No.: WO2017/002826
PCT Pub. Date: Jan. 5, 2017

(65) Prior Publication Data
US 2018/0154097 A1     Jun. 7, 2018

(30) Foreign Application Priority Data

Jun. 29, 2015 (JP) .............................. JP2015-130099
Feb. 12, 2016 (JP) ................................. 2016-025125

(51) Int. Cl.
*A61M 16/00* (2006.01)
*A61B 5/1455* (2006.01)
(Continued)

(52) U.S. Cl.
CPC ......... *A61M 16/024* (2017.08); *A61B 5/1455* (2013.01); *A61B 5/6803* (2013.01);
(Continued)

(58) Field of Classification Search
CPC .............. A61M 16/024; A61M 16/026; A61M 16/022; A61M 16/021; A61M 16/0057;
(Continued)

(56) References Cited

U.S. PATENT DOCUMENTS 5,433,205 A * 7/1995 Visveshwara ............ A61B 8/06
600/455
5,752,509 A     5/1998 Lachmann et al.
(Continued)

FOREIGN PATENT DOCUMENTS

JP 2007-525267 A 9/2007
JP 2007-531592 A 11/2007
(Continued)

OTHER PUBLICATIONS

Communication, dated May 3, 2018, issued by the European Patent Office in counterpart European Application No. 16817934.9.
(Continued)

*Primary Examiner* — Kendra D Carter
*Assistant Examiner* — Brian T Khong
(74) *Attorney, Agent, or Firm* — Sughrue Mion, PLLC

(57) ABSTRACT

A positive pressure therapy device for congestive heart failure includes: a pressure raising unit configured to raise a pressure of an air or a gas mixture of the air and other gases to a positive pressure; an introducing unit configured to introduce the air or the gas mixture that is set to a positive pressure into the airway of a patient; and a blood oxygen level measuring unit configured to measure a value of a blood oxygen level of the patient. A control unit monit is configured to control the pressure raising unit based on the value of the blood oxygen level that is measured by the blood oxygen level measuring unit.

18 Claims, 13 Drawing Sheets

(51) Int. Cl.
 *A61B 5/00* (2006.01)
 *A61M 16/06* (2006.01)

(52) U.S. Cl.
 CPC ........ *A61M 16/0057* (2013.01); *A61M 16/06* (2013.01); *A61B 5/14551* (2013.01); *A61M 2016/003* (2013.01); *A61M 2016/0027* (2013.01); *A61M 2205/3303* (2013.01); *A61M 2205/3344* (2013.01); *A61M 2230/04* (2013.01); *A61M 2230/06* (2013.01); *A61M 2230/205* (2013.01); *A61M 2230/42* (2013.01)

(58) Field of Classification Search
 CPC ...... A61M 16/0069; A61M 2016/0027; A61M 2016/003; A61M 2205/33; A61M 2205/3303; A61M 2205/3306; A61M 2205/3331; A61B 5/1455; A61B 5/14551; A61B 5/14542; A61B 5/68
 See application file for complete search history.

(56) References Cited

U.S. PATENT DOCUMENTS

| | | | | |
|---|---|---|---|---|
| 2005/0126578 | A1* | 6/2005 | Garrison | A61H 9/0078 128/874 |
| 2007/0000494 | A1* | 1/2007 | Banner | A61B 5/0205 128/204.23 |
| 2008/0066753 | A1* | 3/2008 | Martin | A61M 16/0051 128/204.23 |
| 2008/0178880 | A1* | 7/2008 | Christopher | A61M 16/0051 128/204.23 |
| 2008/0190430 | A1* | 8/2008 | Melker | A61B 5/4884 128/204.23 |
| 2009/0014001 | A1* | 1/2009 | Myklebust | A61M 16/12 128/204.18 |
| 2009/0241956 | A1* | 10/2009 | Baker, Jr. | A61M 16/12 128/204.23 |
| 2009/0241958 | A1* | 10/2009 | Baker, Jr. | A61M 16/0051 128/204.23 |
| 2011/0077474 | A1* | 3/2011 | Huiku | A61B 5/02416 600/301 |
| 2011/0257549 | A1 | 10/2011 | Wysocki et al. | |
| 2012/0071729 | A1* | 3/2012 | Doyle | A61B 5/14551 600/301 |
| 2013/0312754 | A1* | 11/2013 | Garde | A61M 16/024 128/204.23 |
| 2014/0076317 | A1* | 3/2014 | Lotz | A61M 16/06 128/204.23 |
| 2015/0034082 | A1* | 2/2015 | Kimm | A61M 16/0051 128/202.16 |
| 2015/0101609 | A1 | 4/2015 | Melker et al. | |

FOREIGN PATENT DOCUMENTS

| | | |
|---|---|---|
| JP | 2008-515494 A | 5/2008 |
| JP | 2014-518645 A | 8/2014 |

OTHER PUBLICATIONS

Communication, dated Jul. 3, 2018, issued by the Japanese Patent Office in counterpart Japanese Application No. 2017-526380.
International Search Report for PCT/JP2016/069181 dated Oct. 4, 2016 [PCT/ISA/210].
Communication, dated Aug. 5, 2019, issued by the Russian Patent Office in counterpart Russian Application No. 2018103056.
Communication, dated Sep. 12, 2019, issued by the State Intellectual Property Office of People's Republic of China, in corresponding Patent Application No. 201680037830.9.

* cited by examiner

[Fig. 1]
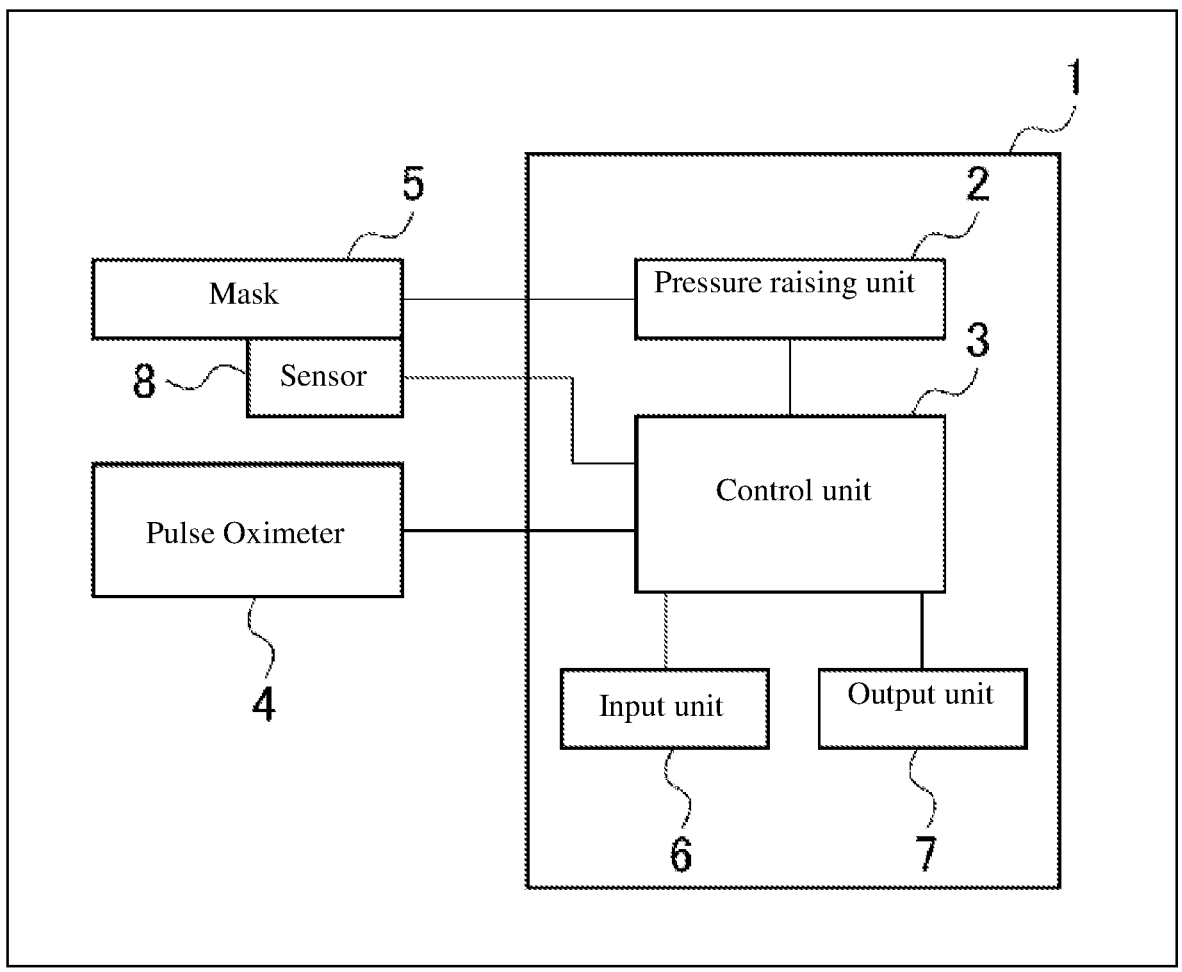

[Fig. 3]
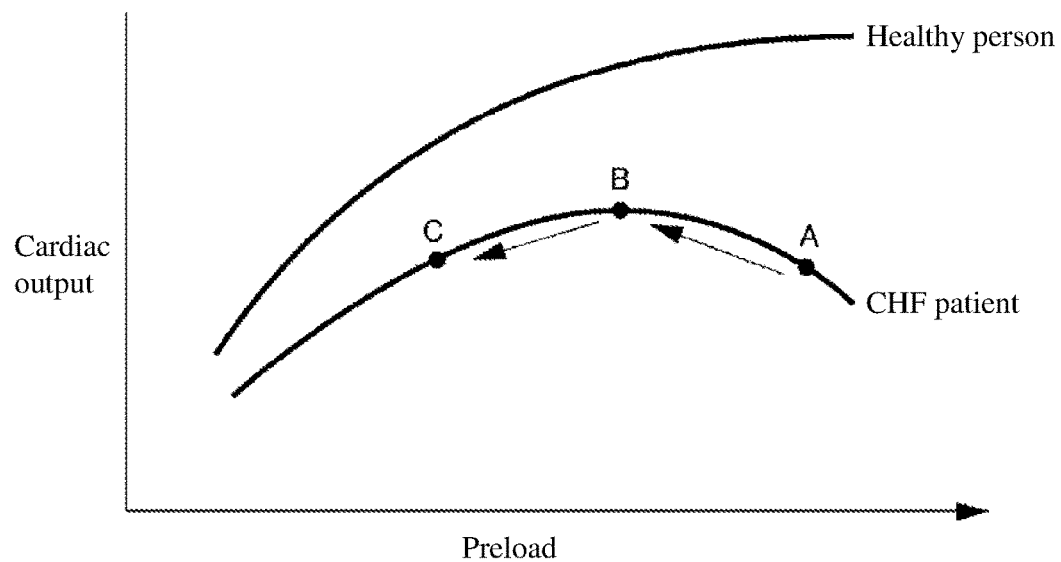

CONGESTIVE HEART FAILURE THERAPY DEVICE WITH POSITIVE PRESSURE ADJUSTMENT

CROSS REFERENCE TO RELATED APPLICATIONS

This application is a National Stage of International Application No. PCT/JP2016/069181, filed on Jun. 28, 2016, which claims priority from Japanese Patent Application No. 2015-130099, filed on Jun. 29, 2015, and Japanese Patent Application No. 2016-025125, filed on Feb. 12, 2016, the contents of all of which are incorporated herein by reference in their entirety.

TECHNICAL FIELD

The present invention relates to an apparatus for use in positive pressure therapy using a face mask respirator for congestive heart failure (CHF) patients.

BACKGROUND ART

Positive pressure therapy using a face mask respirator has drawn attention as a treatment method that improves the symptoms of CHF patients. This treatment method improves the symptoms of CHF by feeding air or a gas mixture of air and other gases with pressure raised to a positive pressure to the airway through a mask that the patient wears on his/her nose or mouth using a positive pressure therapy device such as a noninvasive positive pressure ventilation (NPPV) device, and applying positive pressure to the lungs throughout the entire process of spontaneous respiration.

FIG. 9 shows an example of the change over time of the percutaneous oxygen saturation (SpO2) and the pulse rate of a CHF patient during sleep. The SpO2 and the pulse rate of a healthy person are kept almost constant during sleep, whereas the SpO2 of a CHF patient during sleep may keep decreasing over a long time due to the decubitus position, as shown in FIG. 9. A compensatory mechanism may act to increase the pulse rate, depending on the severity of CHF. One of the reasons of reduction of SpO2 is thought to be an increase in venous return (preload) due to the decubitus position of the CHF patient and reduction of gas exchange in the lungs due to the resultant pulmonary congestion. If the reduction of SpO2 continues for a long time, symptoms such as paroxysmal nocturnal dyspnea and orthopnea may appear.

It is said that the pulse rate reflects the heart rate, and thus in the present description, a description physiologically related to a change in the heart rate is provided using the pulse rate which can be readily measured, for example, with a pulse oximeter.

In positive pressure therapy for CHF patients, a positive pressure therapy device applies positive end expiratory pressure (PEEP) to the patient's lungs in order to improve pulmonary congestion due to circulatory failure. When the positive pressure therapy device applies PEEP to expand the lungs, the intrathoracic pressure rises and the preload decreases, thereby alleviating pulmonary congestion due to circulatory failure. Positive pressure therapy devices that apply PEEP are disclosed in PTL 1 and 2.

When applying PEEP to the lungs of a CHF patient with the positive pressure therapy device, health professionals such as doctors determine PEEP depending on the state of the day of the CHF patient, based on their experiences. However, it is difficult to adjust PEEP finely depending on the state of the CHF patient because the optimum range of PEEP varies with the patient's state such as daily physical conditions.

When a CHF patient uses a positive pressure therapy device at home or outside the home, it is common to use the device without changing the PEEP until the next medical examination. Thus, there is a problem that the PEEP adjusted depending on the daily preload conditions of the CHF patient is thus not applied by the positive pressure therapy device.

CITATION LIST

Patent Literature

[PTL 1]
Japanese Unexamined Patent Application Publication (Translation of PCT Application) No. 2007-525267
[PTL 2]
Japanese Unexamined Patent Application Publication (Translation of PCT Application) No. 2007-531592

SUMMARY OF INVENTION

Technical Problem

The present invention is made in view of the aforementioned problem and an object of the present invention is to provide a congestive heart failure therapy device that applies a positive pressure adjusted within an optimum range depending on the daily preload state of a CHF patient.

Another object of the present invention is to provide a positive pressure value computing device that computes a positive pressure value within such an optimum range.

Solution to Problem

The present invention provides a positive pressure therapy device for congestive heart failure patients. The positive pressure therapy device includes a pressure raising unit configured to raise pressure of air or a gas mixture of air and other gases to a positive pressure, an introducing unit configured to introduce the air or the air mixture set to a positive pressure into the airway of a patient, at least one of a blood oxygen level measuring unit configured to measure a blood oxygen level of the patient or a blood flow rate measuring unit configured to measure a blood flow rate, and a control unit. The control unit controls the pressure raising unit based on the value of the measured blood oxygen level or the value of the blood flow rate.

Hereinafter, the positive pressure therapy device of the present invention may be referred to as "congestive heart failure therapy device".

Three portions included in the congestive heart failure therapy device of the present invention, namely, the pressure raising unit and the introducing unit; sensors such as the blood oxygen level measuring unit and the blood flow rate measuring unit; and the control unit, need not be physically coupled to each other. As for relationship between such sensors and the control unit, it suffices that information of measured values is transmitted from the former to the latter and the control unit suffices to control the pressure raising unit. More specifically, such information transmission and control may have an embodiment of wired or wireless transmission of electrical signals.

Also, the present invention is a positive pressure value computing device for use in a positive pressure therapy for a congestive heart failure patient, comprising: an input unit configured to acquire, as an input value, a value selected from a value of blood oxygen level, a value of blood flow rate and a value of cardiac output of the patient; a positive pressure value computing unit configured to compute a positive pressure value to be applied to the patient based on the input value; and a positive pressure value output unit configured to output a positive pressure value as a computation result.

The positive pressure value computing device of the present invention can be used, for example, as part of the control unit in the congestive heart failure therapy device of the present invention.

Advantageous Effects of Invention

The present invention enables provision of a congestive heart failure therapy device that applies a positive pressure adjusted within an optimum range depending on the daily preload state of a CHF patient.

The present invention provides a positive pressure value within such an optimum range.

BRIEF DESCRIPTION OF DRAWINGS

FIG. 1 is a diagram showing a first embodiment of a congestive heart failure therapy device of the present invention.

FIG. 3 is a diagram showing the relation between preload and cardiac output according to the Frank-Starling law.

DESCRIPTION OF EMBODIMENTS

Figure 2A:
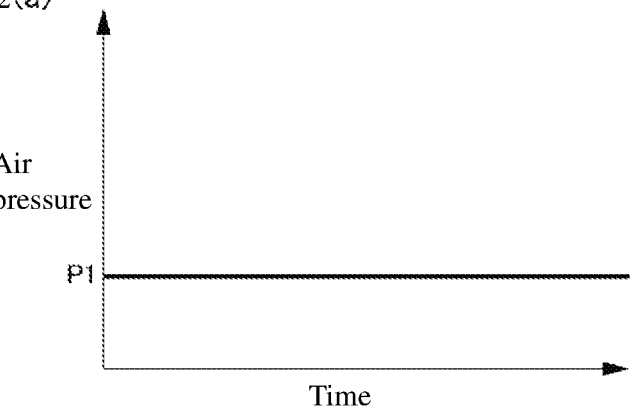
FIGS. 2(a) to 2(c) are diagrams illustrating an air pressure pattern supplied by the congestive heart failure therapy device of the present invention.

The present invention is a positive pressure therapy device for congestive heart failure patients, more specifically a congestive heart failure therapy device that includes a pressure raising unit configured to raise pressure of air or a gas mixture of air and other gases to a positive pressure, an introducing unit configured to introduce the air or the air mixture set to a positive pressure into the airway of a patient, a blood oxygen level measuring unit configured to measure a blood oxygen level of the patient, and a control unit. The control unit controls the pressure raising unit based on the value of the measured blood oxygen level measured by the blood oxygen level measuring unit.

The control unit in the present invention may be a type of control that controls the pressure raising unit such that the positive pressure is raised or lowered when the value of the blood oxygen level is equal to or smaller than a certain value.

The blood oxygen level measuring unit in the present invention may be a pulse oximeter, and the blood oxygen level may be percutaneous oxygen saturation (SpO2).

The present invention provides a positive pressure therapy device for a CHF patient, which is a congestive heart failure therapy device including a pressure raising unit for raising pressure of air or a gas mixture of air and other gases to a positive pressure, an introducing unit for introducing the air or the gas mixture with pressure raised to a positive pressure into the airway of the patient, a blood flow rate measuring unit for measuring the blood flow rate of the patient or a cardiac output measuring unit for measuring the cardiac output of the patient, and a control unit. The control unit controls the pressure raising unit based on the value of the blood flow rate measured by the blood flow rate measuring unit or the value of the cardiac output measured by the cardiac output measuring unit.

The control unit in the present invention may be a type of control that controls the pressure raising unit such that the positive pressure is raised or lowered when the value of the blood flow rate or the cardiac output is equal to or smaller than a certain value.

The positive pressure in the present invention may be positive end expiratory pressure (PEEP).

In the present invention, a width for raising or lowering the positive pressure may be a value set in advance optionally.

The present invention may further include a pulse measuring unit for measuring the pulse of the patient, and the control unit may control the pressure raising unit based on the pulse rate measured by the pulse measuring unit.

The present invention may further include a breath measuring unit for measuring the breath of the patient, and the control unit may control the pressure raising unit based on the respiratory rate measured by the breath measuring unit.

Embodiments of the present invention will be described in detail below with reference to the drawings. The same elements are denoted and described with the same reference signs throughout the description of embodiments.

A configuration of the congestive heart failure therapy device according to the first embodiment of the present invention is shown in FIG. 1. The congestive heart failure therapy device includes main body 1, pulse oximeter 4, mask 5, and sensor 8 provided in mask 5 for measuring the breath of a patient. Main body 1 includes pressure raising unit 2, control unit 3, input unit 6, and output unit 7.

Pulse oximeter 4 is attached to, for example, the patient's finger to serve as a blood oxygen level measuring unit for measuring the percutaneous oxygen saturation (SpO2) as a blood oxygen level and as a pulse measuring unit for measuring the pulse. Sensor 8 is a breath measuring unit and is disposed, for example, in mask 5 to detect at least one of flow velocity, flow rate, and pressure of the patient's exhalation and inhalation and thus measure the breath. Control unit 3 controls pressure raising unit 2 based on information from pulse oximeter 4 and sensor 8.

Pressure raising unit 2 raises the pressure of air or a gas mixture of air and other gases to a positive pressure under an instruction from control unit 3 and supplies the pressure-raised air or gas mixture (which hereinafter may be referred to as "positive pressure air") to mask 5 connected through, for example, a tube. Mask 5 is attached to the nose and/or mouth of a CHF patient to serve as an introducing unit for introducing the positive pressure air into the patient's airway and feeds the positive pressure air to the CHF patient's lungs to apply PEEP.

Control unit 3 acquires information such as flow rate and pressure of the positive pressure air supplied from pressure raising unit 2 to mask 5 using a flow rate sensor, a pressure sensor, or the like and controls pressure raising unit 2 such that the positive pressure air under a predetermined condition is supplied to mask 5. In the congestive heart failure therapy device of the first embodiment, control unit 3 controls pressure raising unit 2 such that the positive pressure air, for example, in modes (a) to (c) as shown in FIGS. 2(*a*) to 2(*c*) is supplied to mask 5.

In mode (a) in FIG. 2(*a*), the positive pressure air with a constant air pressure P1 is supplied throughout the entire period of spontaneous respiration. The PEEP applied to the CHF patient in this mode is at P1. In modes (b) and (c) in FIGS. 2(*b*) and 2(*c*), the positive pressure air with the air pressure periodically varying between P1 and P2 is supplied in synchronization with breath of the CHF patient. Control unit 3 acquires information of the timing of the CHF patient's exhalation and inhalation from sensor 8 provided in mask 5 and controls pressure raising unit 2 such that the air pressure is at P1 during exhalation and at P2 during inhalation. The PEEP applied to the CHF patient in modes (b) and (c) in FIGS. 2(*b*) and 2(*c*) is at P1.

Control unit 3 adjusts P1 in modes (a) to (c) in FIGS. 2(*a*) to 2(*c*) based on the SpO2 and the pulse rate measured by pulse oximeter 4 and the value of respiratory rate measured by sensor 8 and controls pressure raising unit 2 such that PEEP within an optimum range for the CHF patient is applied.

Control unit 3 may be configured to perform control such that PEEP falls within an optimum range based on all of the values of SpO2, pulse rate, and respiratory rate or may be configured to perform control using some of these pieces of information.

The settings of the congestive heart failure therapy device are made by input unit 6, and information such as setting status and operating status of the congestive heart failure therapy device is displayed or output by output unit 7. Biological information (for example, one or more of SpO2, pulse rate, and respiratory rate) of the patient may be output to output unit 7.

The control of pressure raising unit 2 by control unit 3 for applying PEEP adjusted within an optimum range depending on the state of a CHF patient is described as follows.

FIG. 3 illustrates how the cardiac output changes with increase in the preload for a healthy person and a CHF patient, based on the Frank-Starling's law. In the healthy person, the cardiac systole and diastole increases with increase in the preload, thereby increasing the cardiac output.

However, since the ability in stretching and contraction of cardiac muscle is declined in the CHF patient, the cardiac output does not increase anymore and often decreases when the preload exceeds a certain value (point B in FIG. 3). Because of this, blood may accumulate in the lungs to cause pulmonary congestion. For example, the preload increases in the decubitus position, and in the case of a CHF patient that developed pulmonary congestion through the mechanism described above, a reduction of SpO2 over a long time during sleep at night, an increase in the pulse rate, an increase in the respiratory rate and so on may occur as shown in FIG. 9.

In the positive pressure therapy, PEEP is applied using the congestive heart failure therapy device, for example, to a CHF patient with a preload at point A in FIG. 3. When PEEP is applied to raise the intrathoracic pressure, the venous return decreases and the preload moves in the direction from point A to point B, thereby increasing the cardiac output and improving circulatory failure. However, since the state of preload of a CHF patient varies depending on the daily physical condition, even if a PEEP set on a certain day may be able to adjust the cardiac output to point B in FIG. 3, the same PEEP may not result in a cardiac output in the vicinity of the top of the curve on another day. For example, in a case where the preload before the start of current treatment is smaller than the preload before the start of previous treatment, a treatment at the PEEP value in the previous treatment at which the cardiac output was adjusted to the peak of the curve, point B, would adjust the cardiac output further to the left side beyond point B.

Figure 9:
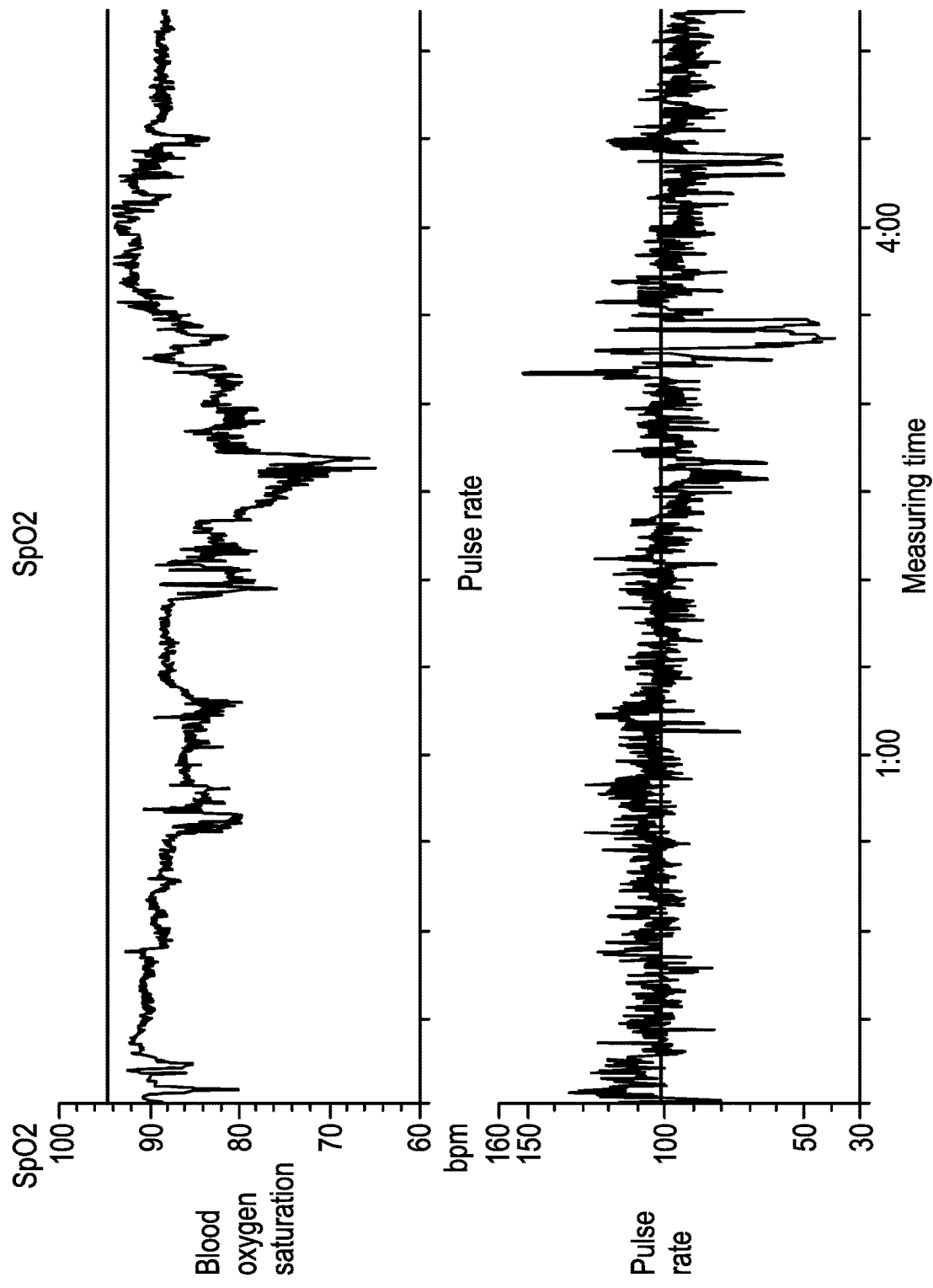
FIG. 9 is a diagram showing the SpO2 and the pulse rate of a CHF patient during sleep before the congestive heart failure therapy device is applied in Example 1.

As described above, even if the PEEP of the congestive heart failure therapy device is once adjusted to an optimum range, another optimum cardiac output will not be achieved unless PEEP is readjusted based on the daily preload state of the CHF patient, and pulmonary congestion and reduction of SpO2 attributable thereto as shown in FIG. 9 may occur. Therefore, in the first embodiment of the present invention, control unit 3 monitors the SpO2 of a CHF patient with pulse oximeter 4 and, when a state in which the SpO2 is below a preset value K (for example, 90%) lasts for a certain period of time, control unit 3 determines that the applied PEEP is not appropriate for the present state of the patient and instructs pressure raising unit 2 to change PEEP, that is, P1.

When control unit 3 of the congestive heart failure therapy device adjusts PEEP based on the measured SpO2, PEEP within an optimum range based on the daily preload state is applied to a CHF patient. A preset value of SpO2 serving as a reference and the duration of a state in which the SpO2 is below the preset value are input to control unit 3 in advance and can be changed as appropriate.

Figure 4:
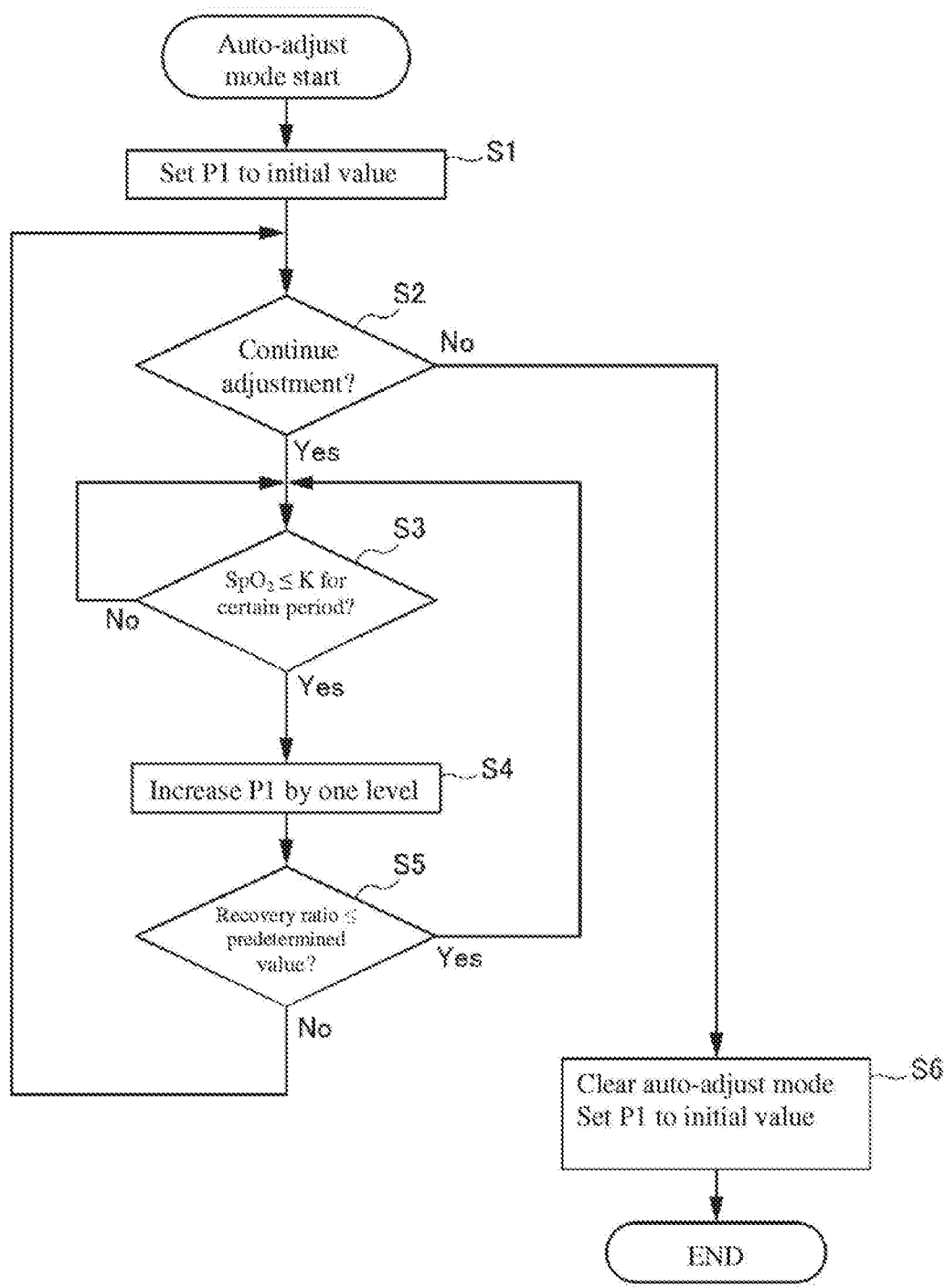
FIG. 4 is a diagram showing an example of the control method by the control unit in the first embodiment.

An example of the control method by control unit 3 of the congestive heart failure therapy device will be described based on FIG. 4.

The CHF patient receiving the positive pressure therapy sets the congestive heart failure therapy device to the PEEP automatic adjustment mode. Control unit 3 controls pressure raising unit 2 such that positive pressure air is supplied to mask 5 in a mode selected from (a) to (c) shown in FIGS. 2(*a*) to 2(*c*). The positive pressure air is supplied to the lungs by the congestive heart failure therapy device, and PEEP, that is P1, is applied to the CHF patient at the end of expiration. Control unit 3 acquires information of the SpO2 and the pulse rate of the CHF patient from pulse oximeter 4 and acquires information of the respiratory rate from sensor 8.

When automatic adjustment mode is started, first of all, control unit 3 sets P1 as an initial value of PEEP (step S1). The initial value of PEEP is set to a lowest value within a range in which reduction of preload of the CHF patient can be expected, considering that the preload state of the CHF patient changes daily and PEEP higher than necessary has a risk of reducing the cardiac output as shown in FIG. 3. The initial value of PEEP at the start of the automatic adjustment mode may be a value stored by the congestive heart failure therapy device when the last treatment is finished. However, when the preload before the start of current treatment is smaller than in the previous treatment, PEEP higher than necessary will be applied. In order to avoid such a risk, a value obtained by subtracting a predetermined value from the last adjustment value stored by the congestive heart failure therapy device may be employed.

Next, control unit 3 determines whether to continue adjustment of PEEP (step S2). When the control unit determines to continue the adjustment, the control proceeds to step S3 and the value of SpO2 is monitored. The detail of the determination in step S2 will be described later.

If control unit 3 detects that a state in which the value of SpO2 is reduced to a preset value of K lasts for a certain period (step S3), control unit 3 determines that PEEP applied to the CHF patient is not appropriate for the present preload state and instructs pressure raising unit 2 to increase the PEEP value P1 by one level (step S4). Here, the pressure difference of one level is a value preset optionally in advance and is preferably set in a range, for example, from 9.8 Pa to 49 Pa (0.1 to 0.5 cmH$_2$O). A plurality of such levels may be set, and in this case, the pressure differences of each level may be the same or may be different.

SpO2 is known to repeatedly decrease and increase in a short term due to the effects of diseases other than CHF, for example, repetition of closing and opening of the airway in obstructive sleep apnea syndrome. In order to avoid a determination error due to such effects, the average value of SpO2 in a short term, preferably, in a term of a few minutes may be compared with the average value of SpO2 in a long term, preferably in a term of a few tens of minutes.

After pressure raising unit 2 increases the PEEP value P1 by one level, control unit 3 measures the value of SpO2 after the elapse of preset time and obtains the recovery ratio (step S5). If the recovery ratio of SpO2 value resulting from the increase in the PEEP value is equal to or smaller than a predetermined value, control unit 3 determines that adjustment has been made to a position closer to point B between point A and point B in FIG. 3, that is, to PEEP within an optimum range, and monitors the value of SpO2 after returning to step S3 without further changing the PEEP value P1.

If the recovery ratio of the SpO2 value is not equal to or smaller than a predetermined value in step S5, the control returns to step 2. Control unit 3 then determines whether to continue adjustment of PEEP. For example, in step 2, control unit 3 examines information of the pulse rate from pulse oximeter 4 and information of the respiratory rate from sensor 8. When an increase equal to or higher than a certain width is observed in at least one of the pulse rate and the respiratory rate, there is a possibility that, as a result of increasing P1 by one level in step S4, a compensatory mechanism could have acted to increase the heart rate and compensate for the cardiac output, or to increase the respiratory rate and compensate for reduction in the blood oxygen level. In such a case, control unit 3 abandons elimination of circulatory failure by adjustment of PEEP for the safety of the CHF patient.

Including a state in which the cardiac output is reduced by excessive PEEP, the compensatory mechanism may also fail depending on the state and complications of the CHF patient, and the pulse rate or the respiratory rate may exhibit a variation equal to or greater than a certain width. The automatic adjustment may be cancelled when a variation equal to or greater than a certain width is observed in at least one of the pulse rate and the respiratory rate.

If the adjustment of PEEP is abandoned in step S2, control unit 3 resets PEEP to the initial value that is the lowest value within the range in which reduction of preload can be expected in the CHF patient, and clears the automatic adjustment mode (step S6). The abandonment of elimination of circulatory failure by adjustment of PEEP is displayed on output unit 7 to prompt for an examination by doctors or the like.

If an increase or a decrease equal to or greater than a certain width is not observed in the pulse rate or the respiratory rate in step S2, control unit 3 determines that adjustment is on the way from point A to the peak of the curve, point B, shown in FIG. 3, and continues the adjustment after proceeding to step S3.

In this way, in the congestive heart failure therapy device, since control unit 3 adjusts the PEEP value P1 based on the value of SpO2, even when a range of optimum PEEP varies depending on the daily preload state of the CHF patient, control unit 3 can apply PEEP automatically adjusted within the range.

For all or any of SpO2, pulse rate, and respiratory rate serving as the patient's biological information used by control unit 3 for the control of PEEP, a plurality of data measured in succession may be subjected to averaging process and used. This is applicable to other embodiments and examples described below.

Another example of the control method in the congestive heart failure therapy device in the first embodiment will be described based on FIG. 5. In another example of the control method, control is added in which PEEP is gradually reduced and a state close to point B is attained when control unit 3 determines that the control is in a state on point C side in FIG. 3.

When automatic adjustment mode is started, first of all, control unit 3 sets P1 to an initial value that is the lowest value within a range in which reduction of preload can be expected in the CHF patient (step S11). Next, if the automatic adjustment mode-emergency release condition described later is not satisfied and control unit 3 determines to continue the adjustment (step S12), the control proceeds to step S13 where the value of SpO2 is monitored. In step S13, if control unit 3 detects that a state in which the value of SpO2 is lower than the preset value K lasts for a certain period, it determines that PEEP is not appropriate, and instructs pressure raising unit 2 to increase the PEEP value P1 by one level (step S14).

After pressure raising unit 2 increases the PEEP value P1 by one level, control unit 3 compares the value of SpO2 after the elapse of a preset time with the value obtained just before step S14 (step S15). If the value of SpO2 has an increase because of the increase in the PEEP value by one level in step S14, control unit 3 determines that control is on point A side and moving toward point B in FIG. 3 (step S16), and the control then returns to step S12. As long as the value of SpO2 is lower than the preset value K and the value of SpO2 keeps rising, control unit 3 repeatedly instructs pressure raising unit 2 to increase P1 by one level. If the value of SpO2 becomes greater than the preset value K, control unit 3 keeps monitoring of SpO2 while maintaining P1.

On the other hand, if increasing P1 does not raise SpO2 in step S15, the control is advanced to step S17, where automatic adjustment mode-emergency release condition described later is not satisfied and control unit 3 determines whether to continue the adjustment. If control unit 3 determines to continue the adjustment, the control proceeds to step S18. If a state in which the value of SpO2 is lower than the preset value K still lasts for a certain period, it can be assumed that the vicinity of point B in FIG. 3 is reached but the cardiac output does not satisfy the required amount, or that control is beyond point B and moving toward point C. Therefore, control unit 3 instructs pressure raising unit 2 to reduce P1 by one level (step S19). Next, the value of SpO2 is compared with the value just before step S19 (step S20). If the value of SpO2 has a rise, it is determined that control is on point C side and moving toward point B (step S21). The control then returns to step S17, and while the value of SpO2 is lower than the preset value K and the value of SpO2 keeps rising, control unit 3 repeatedly instructs pressure raising unit 2 to reduce P1 by one level. If the value of SpO2 becomes greater than the preset value K, control unit 3 keeps monitoring of SpO2 while maintaining P1.

If the value of SpO2 does not have a rise in step S20, it means a state in which either that the vicinity of point B in FIG. 3 is reached but the cardiac output does not satisfy the required amount, or that effective control to increase the cardiac output toward point B is impossible for some reason. Therefore, control unit 3 abandons elimination of circulatory failure by adjustment of PEEP for the safety of the CHF patient (step S22).

Figure 5:
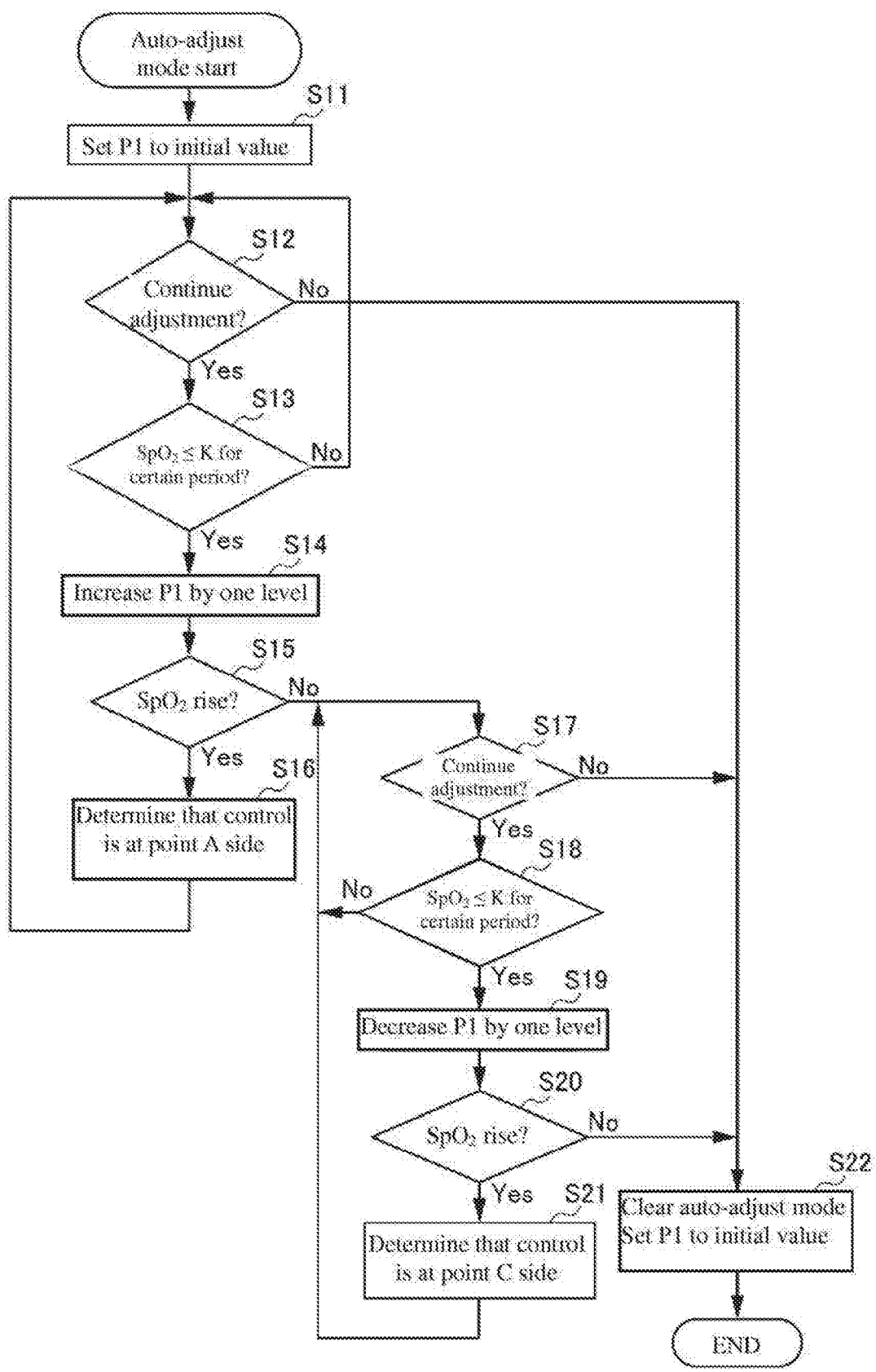
FIG. 5 is a diagram showing another example of the control method by the control unit in the first embodiment.

Control unit 3 monitors the SpO2, the pulse rate, and the respiratory rate throughout the period in which the control in FIG. 5 is performed. Furthermore, an SpO2, a pulse rate, and a respiratory rate are preset in advance as an automatic adjustment mode-emergency release condition in control unit 3. When, compared with the values before the start of the adjustment mode, the value of SpO2 becomes lower than the preset value, or at least one of the pulse rate and the respiratory rate varies by the preset value or greater, control unit 3 determines that the automatic adjustment mode-emergency release condition is satisfied, and clears the adjustment of PEEP urgently for safety.

As described above, when the adjustment of PEEP is abandoned and the automatic adjustment mode is cleared, or the emergency release is activated for the automatic adjustment mode, control unit 3 resets PEEP to the initial value which is the lowest value within a range in which reduction of preload can be expected in the CHF patient. The abandonment of elimination of circulatory failure by adjustment of PEEP is displayed on output unit 7 to prompt for an examination by doctors or the like.

Figure 6:
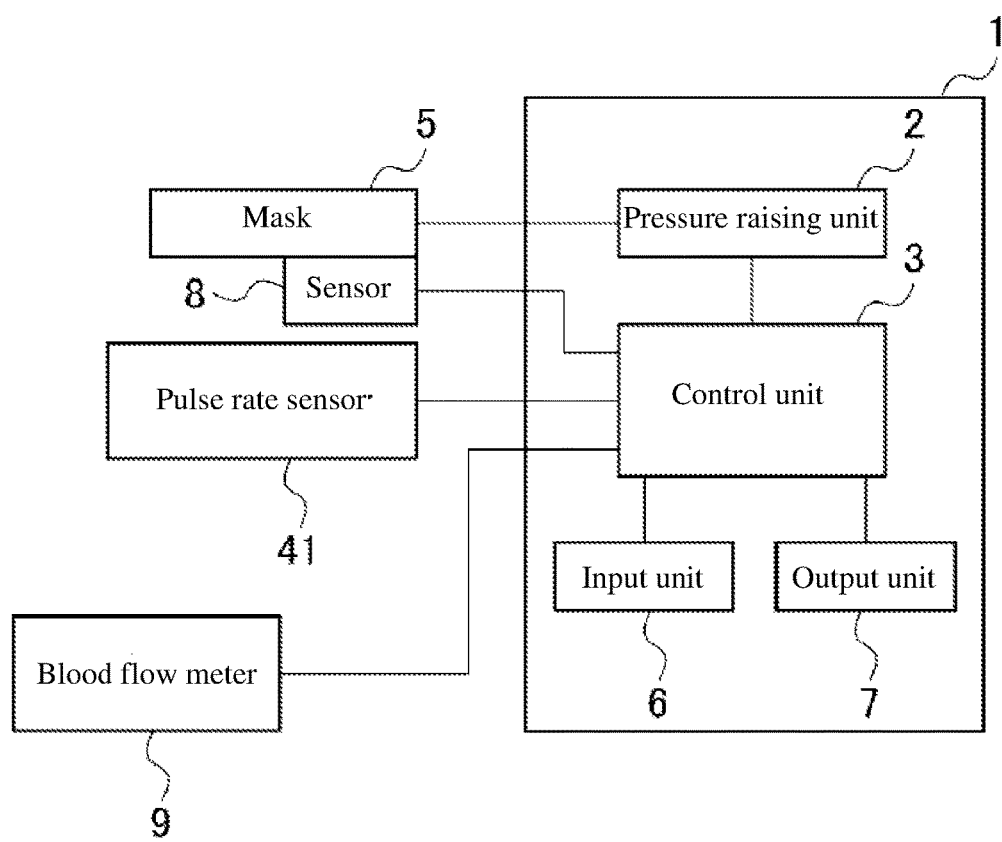
FIG. 6 is a diagram showing a second embodiment of a congestive heart failure therapy device of the present invention.

A configuration of the congestive heart failure therapy device according to the second embodiment of the present invention is shown in FIG. 6. The congestive heart failure therapy device of the second embodiment is provided with blood flow meter 9 as a blood flow rate measuring unit to the congestive heart failure therapy device of the first embodiment shown in FIG. 1.

In a CHF patient, when the cardiac output decreases, the tissue blood flow rate of, for example, finger tips may decrease. As mentioned previously, a decrease in the cardiac output and an increase in the preload cause pulmonary congestion and deteriorate gas exchange in the lungs, which is thought to cause reduction of SpO2 over a long time. PEEP may be controlled accurately using the blood flow rate as a parameter.

Blood flow meter 9 is preferably a laser blood flow meter attached to the patient's finger or the like to enable measurement through the skin surface in an easy and noninvasive manner. Alternatively, a noninvasive blood flow meter such as an ultrasonic blood flow meter and an electromagnetic blood flow meter may be used. Sensor 8 serving as a breath measuring unit may be disposed, for example, in mask 5 to detect at least one of flow velocity, flow rate, and pressure of the patient's exhalation and inhalation and measure the breath.

The pulse rate sensor 41 serving as a pulse measuring unit may be a photoelectric sphygmograph sensor or an electrocardiogram sensor, or a pulse oximeter attached to chest, fingertip, earlobe, wrist, or the like. Alternatively, blood flow rate meter 9 may be used also as a pulse measuring unit to measure a blood flow rate and a pulse.

Figure 2B:
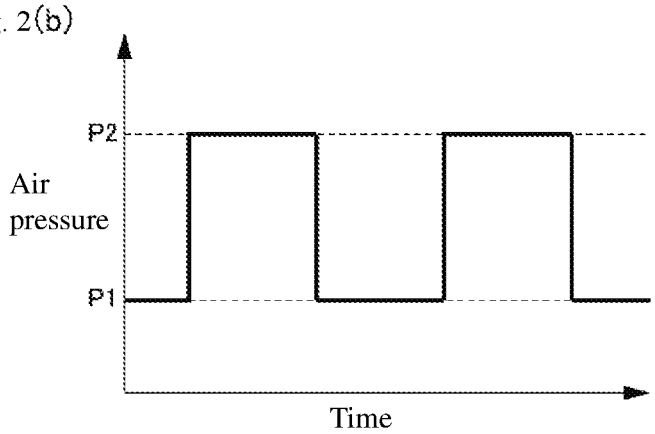
Figure 2C:
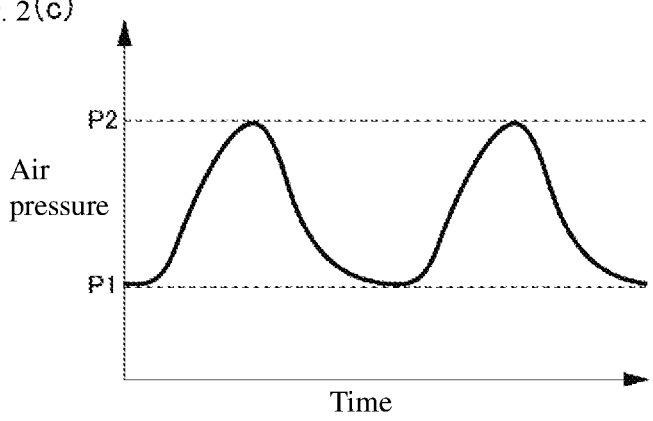

Control unit 3 acquires information such as flow rate and pressure of the positive pressure air supplied to mask 5 via sensor 8 and controls pressure raising unit 2 such that a positive pressure air under a predetermined condition is supplied to mask 5. Control unit 3 controls pressure raising unit 2 so as to supply, for example, positive pressure air in mode (a) to (c) as shown in FIGS. 2(a) to 2(c) to mask 5 and applies PEEP of P1 to a CHF patient.

In the congestive heart failure therapy device of the second embodiment, control unit 3 controls pressure raising unit 2 based on the value of the blood flow rate measured by blood flow meter 9 to adjust PEEP.

Figure 7:
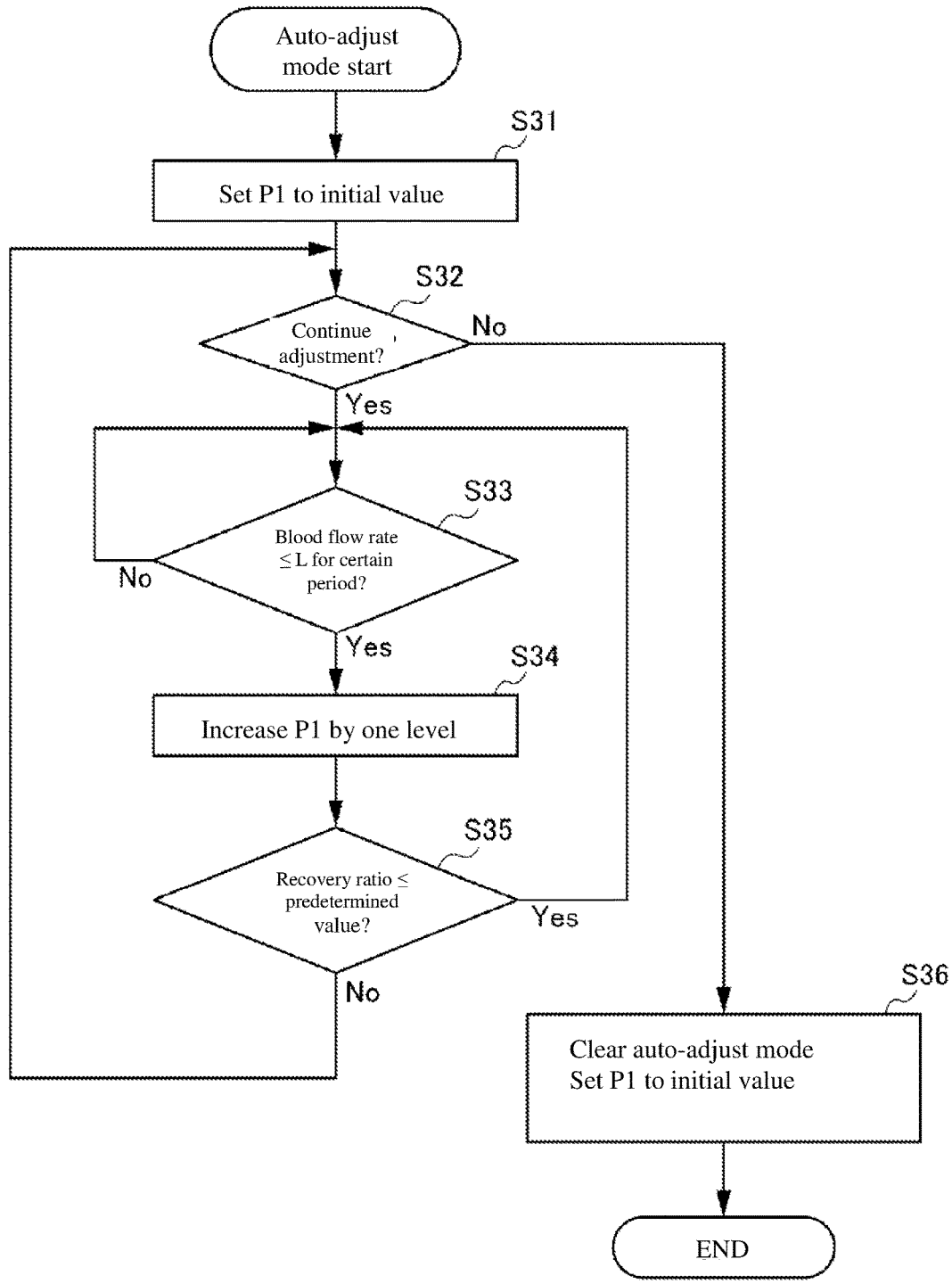
FIG. 7 is a diagram showing an example of the control method by the control unit in the second embodiment.

An example of the control method by control unit 3 is shown in FIG. 7. When automatic adjustment mode starts, control unit 3 sets P1 to an initial value of PEEP (step S31) and controls pressure raising unit 2 so as to supply positive pressure air to mask 5 in a mode selected from (a) to (c) shown in FIGS. 2(a) to 2(c). The initial value of PEEP is set to the lowest value within a range in which reduction of preload of the CHF patient can be expected, considering that the preload state of a CHF patient changes daily and PEEP higher than necessary has a risk of reducing a cardiac output as shown in FIG. 3.

The initial value of PEEP may be a value stored by the congestive heart failure therapy device when the last treatment is finished. However, when the preload before the start of current treatment is smaller than in the previous treatment, PEEP higher than necessary is applied. In order to avoid such a risk, a value obtained by subtracting a predetermined value from the last adjustment value stored by the congestive heart failure therapy device may be employed.

Next, if the automatic adjustment mode-emergency release condition is not satisfied and control unit 3 determines to continue the adjustment (step S32), the control proceeds to step S33. Control unit 3 measures and monitors the value of the blood flow rate sent from blood flow meter 9 at regular intervals, for example, every one second. Then, when control unit 3 detects that a state in which the blood flow rate is lower than the preset value L lasts for a certain period (step S33), it determines that PEEP applied to the CHF patient is not appropriate for the present preload state. Here, the preset value L and the certain period by which reduction of the blood flow rate is determined are values preset in the congestive heart failure therapy device and can be changed as appropriate.

If control unit 3 determines that PEEP is not appropriate for the present state of the patient because a state in which the blood flow rate is reduced lasts for a certain period, it instructs pressure raising unit 2 to increase the PEEP value P1 by one level (step S34).

After pressure raising unit 2 increases the PEEP value P1 by one level, control unit 3 measures a blood flow rate after the elapse of a preset time and obtains the recovery ratio of the blood flow rate (step S35). If the recovery ratio of the blood flow rate resulting from the increase of the PEEP value is equal to or smaller than a predetermined value, control unit 3 determines that adjustment has been made to a position closer to point B between point A and point B in FIG. 3, that is, to PEEP within an optimum range, and monitors the blood flow rate after returning to step S33 without further changing the PEEP value P1.

If the recovery ratio of the blood flow rate is not equal to or smaller than a predetermined value in step S35, control unit 3 determines whether or not to continue adjustment of PEEP (step S32). For example, when a variation equal to or greater than a certain width is observed in at least one of the pulse rate and the respiratory rate, control unit 3 abandons elimination of circulatory failure by adjustment of PEEP for the safety of the CHF patient, judging that the situation corresponds to the automatic adjustment mode-emergency release condition.

If the adjustment of PEEP is abandoned in step S32, control unit 3 resets PEEP to an initial value that is the lowest value within the range in which reduction of preload can be expected in the CHF patient, and clears the automatic adjustment mode (step S36). The abandonment of elimination of circulatory failure by adjustment of PEEP is displayed on output unit 7 to prompt for an examination by doctors or the like.

If a variation equal to or greater than a certain width is not observed in the pulse rate or the respiratory rate in step S32, control unit 3 determines that control is on the way from point A toward the peak of the curve, point B, shown in FIG. 3, and the control returns to step S33 to increase the PEEP value P1 by another one level. The control then proceeds to step S34.

In this way, in the congestive heart failure therapy device of the second embodiment, since control unit 3 adjusts the PEEP value P1 based on the blood flow rate, even when a range of optimum PEEP varies depending on the daily preload state of the CHF patient, control unit 3 can apply PEEP automatically adjusted within the range.

For all or any of blood flow rate, SpO2, pulse rate, and respiratory rate serving as the patient's biological information used by control unit 3 for the control of PEEP, a plurality of data measured in succession may be subjected to averaging processing and used. This is applicable to other embodiments and examples described below.

Another example of the control method in the congestive heart failure therapy device in the second embodiment will be described based on FIG. 8. In another example of the control method, control is added in which PEEP is gradually reduced and a state close to point B is attained when control unit 3 determines that control is in a state at point C side in FIG. 3.

When the automatic adjustment mode is started, first of all, control unit 3 sets P1 to an initial value that is the lowest value within a range in which reduction of preload can be expected in the CHF patient (step S41). Next, control unit 3 determines whether to continue PEEP adjustment (step S42). The determination is based on, for example, the automatic adjustment mode-emergency release condition. When control unit 3 determines to continue adjustment, the control proceeds to step S43. In step S43, if control unit 3 detects that a state in which the value of the blood flow rate is lower than the preset value L lasts for a certain period, it determines that given PEEP is not appropriate, and instructs pressure raising unit 2 to increase the PEEP value P1 by one level (step S44).

After the PEEP value P1 is increased by one level by pressure raising unit 2, control unit 3 compares the value of the blood flow rate after the elapse of a preset time with the value obtained just before step S44 (step 45). If the value of the blood flow rate has a rise, control unit 3 determines that control is at point A side in FIG. 3 and moving toward point B (step S46), it repeatedly instructs pressure raising unit 2 to increase P1 by one level as long as the value of the blood flow rate is lower than the preset value K and the value of the blood flow rate keeps rising. If the value of the blood flow rate becomes greater than the preset value K, control unit 3 keeps monitoring of the blood flow rate while maintaining P1.

On the other hand, if increasing P1 does not raise the value of the blood flow rate in step S45, control unit 3 determines whether the automatic adjustment mode-emergency release condition is satisfied, and judges whether to continue adjustment (step S47). If the adjustment is to be continued, the control proceeds to step S48. If a state in which the value of blood flow rate is lower than the preset value L still lasts for a certain period, it can be assumed that the vicinity of point B in FIG. 3 is reached but the cardiac output does not satisfy the required amount, or that control is beyond point B and moving toward point C. Therefore, control unit 3 instructs pressure raising unit 2 to reduce P1 by one level (step S49).

If the value of the blood flow rate rises as a result of lowering P1 by one level, control unit 3 determines that control is at point C side and moving toward point B (step S51). The control then returns to step S47, and as long as the value of blood flow rate is lower than the preset value L and the value of blood flow rate keeps rising, control unit 3 repeatedly instructs pressure raising unit 2 to reduce P1 by one level. If the value of blood flow rate becomes greater than the preset value L, control unit 3 continues monitoring of blood flow rate while maintaining P1.

If the value of blood flow rate does not rise in step S50, it is assumed that the vicinity of point B in FIG. 3 is reached but the cardiac output does not satisfy the required amount, or that the effective control to increase the cardiac output toward point B is impossible for some reason. Therefore, control unit 3 abandons elimination of circulatory failure by adjustment of PEEP for the safety of the CHF patient (step S52).

Figure 8:
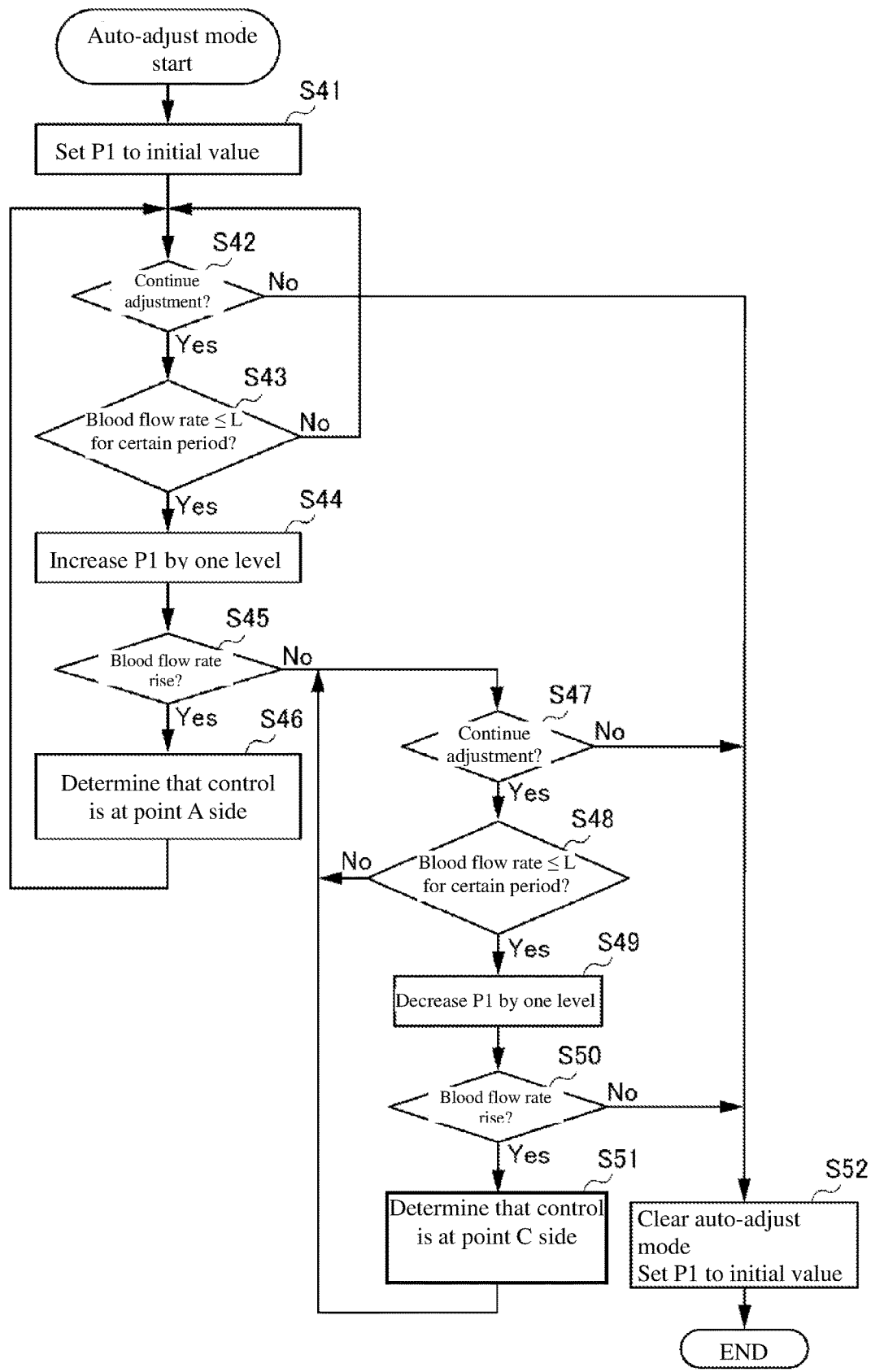
FIG. 8 is a diagram showing another example of the control method by the control unit in the second embodiment.

Control unit 3 monitors a blood flow rate, an SpO2, a pulse rate, and a respiratory rate throughout the period in which the control in FIG. 8 is performed. Furthermore, a blood flow rate, a SpO2, a pulse rate, and a respiratory rate are preset in advance as the automatic adjustment mode-urgent clearing condition in control unit 3. When any of the blood flow rate, the SpO2, the pulse rate, and the respiratory rate varies by the preset value or greater compared with the values before the start of adjustment mode, control unit 3 determines that the automatic adjustment mode-emergency release condition is satisfied, and clears the adjustment of PEEP urgently for safety.

As mentioned previously, when the adjustment of PEEP is abandoned and the automatic adjustment mode is cleared, or the emergency release is activated for automatic adjustment mode, control unit 3 resets PEEP to the initial value. The abandonment of elimination of circulatory failure by adjustment of PEEP is displayed on output unit 7 to prompt for an examination by doctors or the like.

In the second embodiment of the present invention, a change in cardiac output is indirectly obtained from the blood flow rate. However, a cardiac output measuring unit capable of directly measuring the cardiac output may be provided. PEEP can be adjusted more accurately if control unit 3 performs control based on the value of the cardiac output measured by the cardiac output measuring unit. For example, an invasive blood flow meter by the thermodilution method can be used as an cardiac output measuring unit.

Although preferable embodiments of the present invention have been detailed above, the present invention is not limited to the foregoing embodiments and is susceptible to various modifications and changes without departing from the spirit of the present invention recited in the claims.

For example, the control may be configured such that even when SpO2 is equal to or greater than a predetermined reference value (for example 90%), PEEP is controlled when both or one of the pulse rate and the respiratory rate varies by a certain magnitude or greater.

The congestive heart failure therapy device may have the function for manually inputting a rise or a drop of the PEEP value P1 through input unit 6 and displaying on output unit 7 a change in SpO2 or blood flow rate of the CHF patient that is attributable to the rise or drop of PEEP. The provision of such a function enables health professionals such as doctors to obtain a PEEP value within an optimum range while operating the congestive heart failure therapy device to observe changes in SpO2 or blood flow rate in addition to using their own experiences.

EXAMPLES

Example 1

Figure 10:
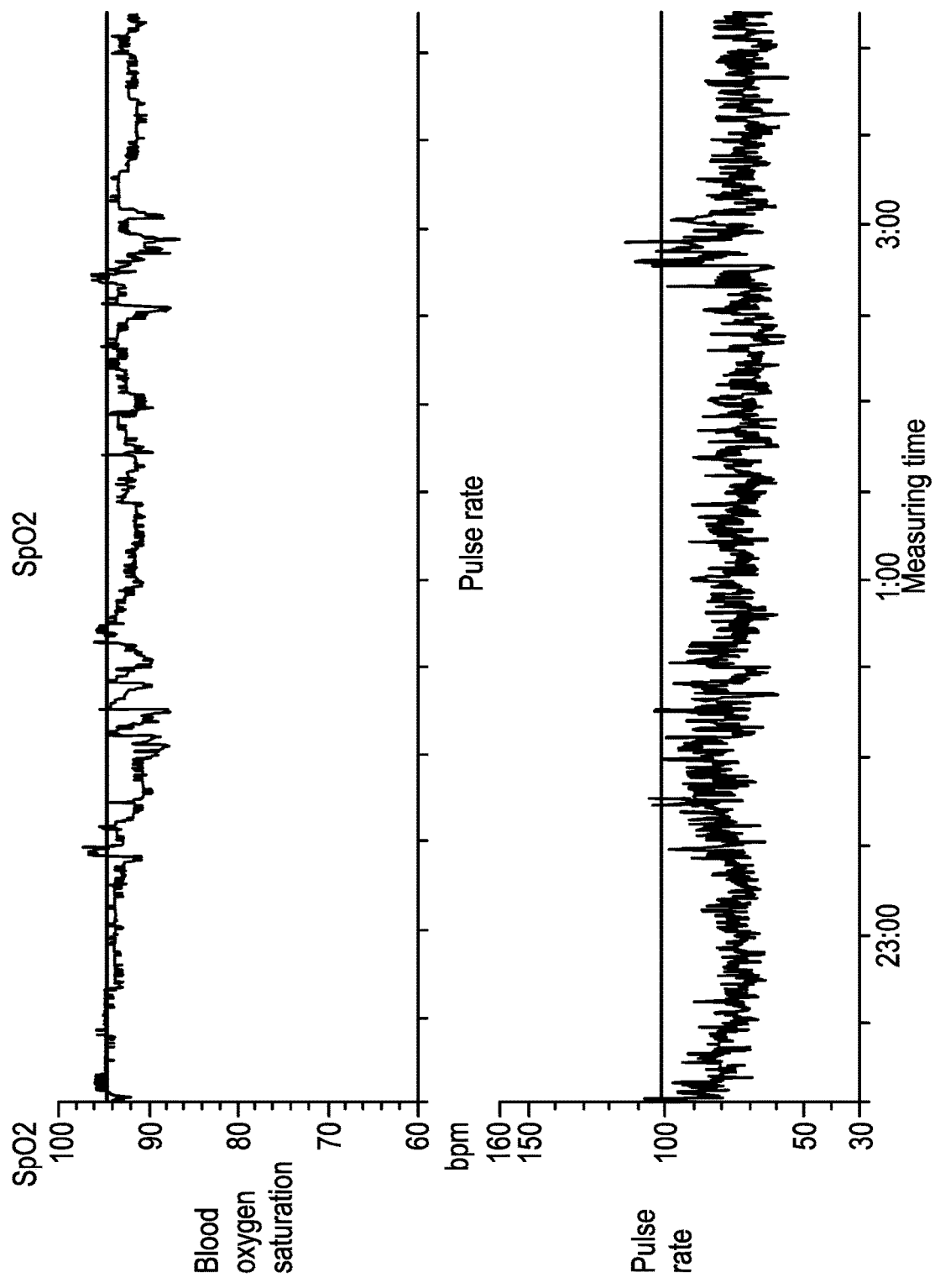
FIG. 10 is a diagram showing the SpO2 and the pulse rate of a CHF patient applied with the congestive heart failure therapy device in Example 1.

FIG. 9 and FIG. 10 show an example of the effect of applying the congestive heart failure therapy device to a CHF patient during sleep. In FIG. 9, the congestive heart failure therapy device is not used, and in FIG. 10, the congestive heart failure therapy device is used. The horizontal axis shows a measuring time. For example, FIG. 9 shows the SpO2 and pulse rate changes of a CHF patient during sleep over time for the period from 23:00 to around 05:30 of. Compared with FIG. 9 in which the congestive heart failure therapy device is not used, FIG. 10 in which the congestive heart failure therapy device is used and PEEP within an optimum range is applied to the patient shows that the SpO2 is maintained at almost 90% or higher and the pulse rate is also maintained at 100 or lower.

Example 2

For an elderly CHF patient who is different from Example 1, a treatment example by the congestive heart failure therapy device will be described in FIG. 11, FIG. 12, and FIG. 13. The dotted line parallel to the horizontal axis of the graph in FIG. 11 to FIG. 13 indicates the line on which the blood oxygen saturation is 90%. The patient has mild emphysema and idiopathic dilatation of pulmonary artery in addition to chronic CHF and undergoes oxygen therapy during sleep at night.

Figure 11:
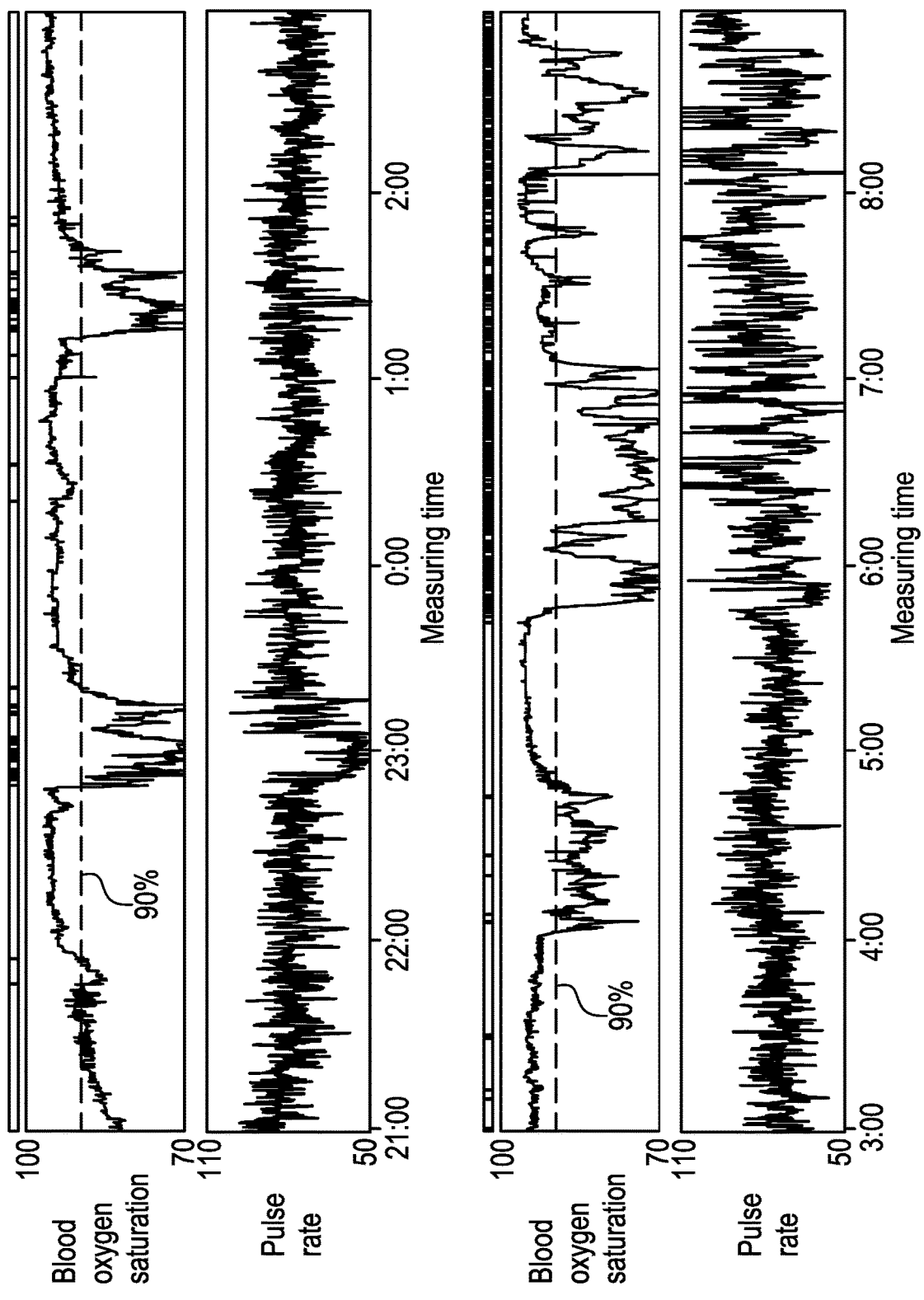
FIG. 11 is a diagram showing the SpO2 and the pulse rate of a CHF patient during sleep before the congestive heart failure therapy device is applied in Example 2.

FIG. 11 shows a state in which 0.5 liter/minute of oxygen is administered to the patient without applying the congestive heart failure therapy device. From 21:00 to 22:00, and from 06:00 to 09:00 next morning, reduction of the base line (the median value after the averaging processing) of SpO2, presumably caused by CHF, is observed. The reduction of SpO2 observed at three points, namely, around 23:00, around 01:30, and past 04:00, which is temporary and has a large amplitude and a short variation cycle, is presumably caused by reduction of breathing effort often observed during muscle relaxation in the REM period and is thought to be different from a SpO2 reduction caused by CHF.

Figure 12:
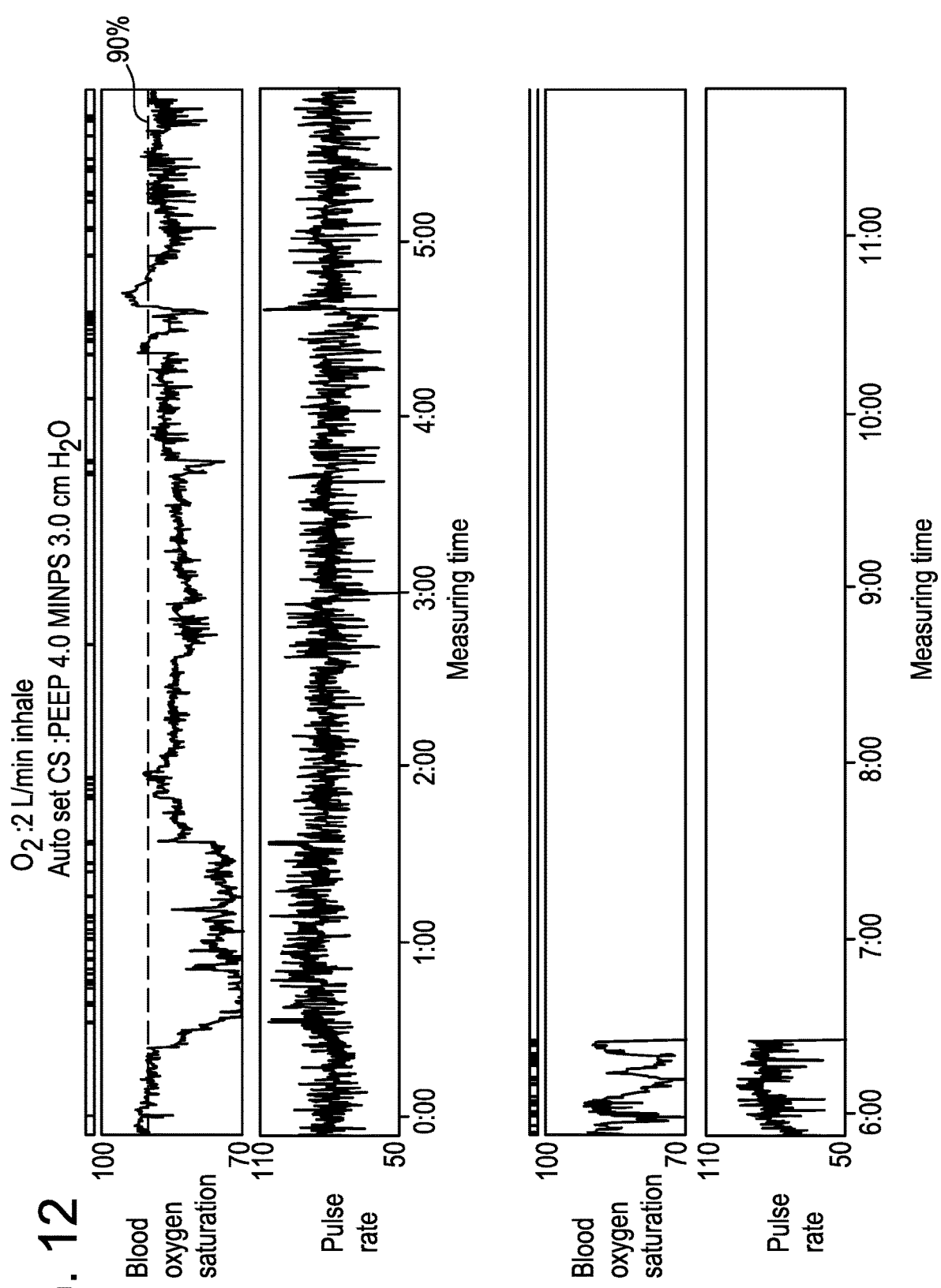
FIG. 12 is a diagram showing the SpO2 and the pulse rate of a CHF patient applied with the congestive heart failure therapy device in Example 2.
Figure 13:
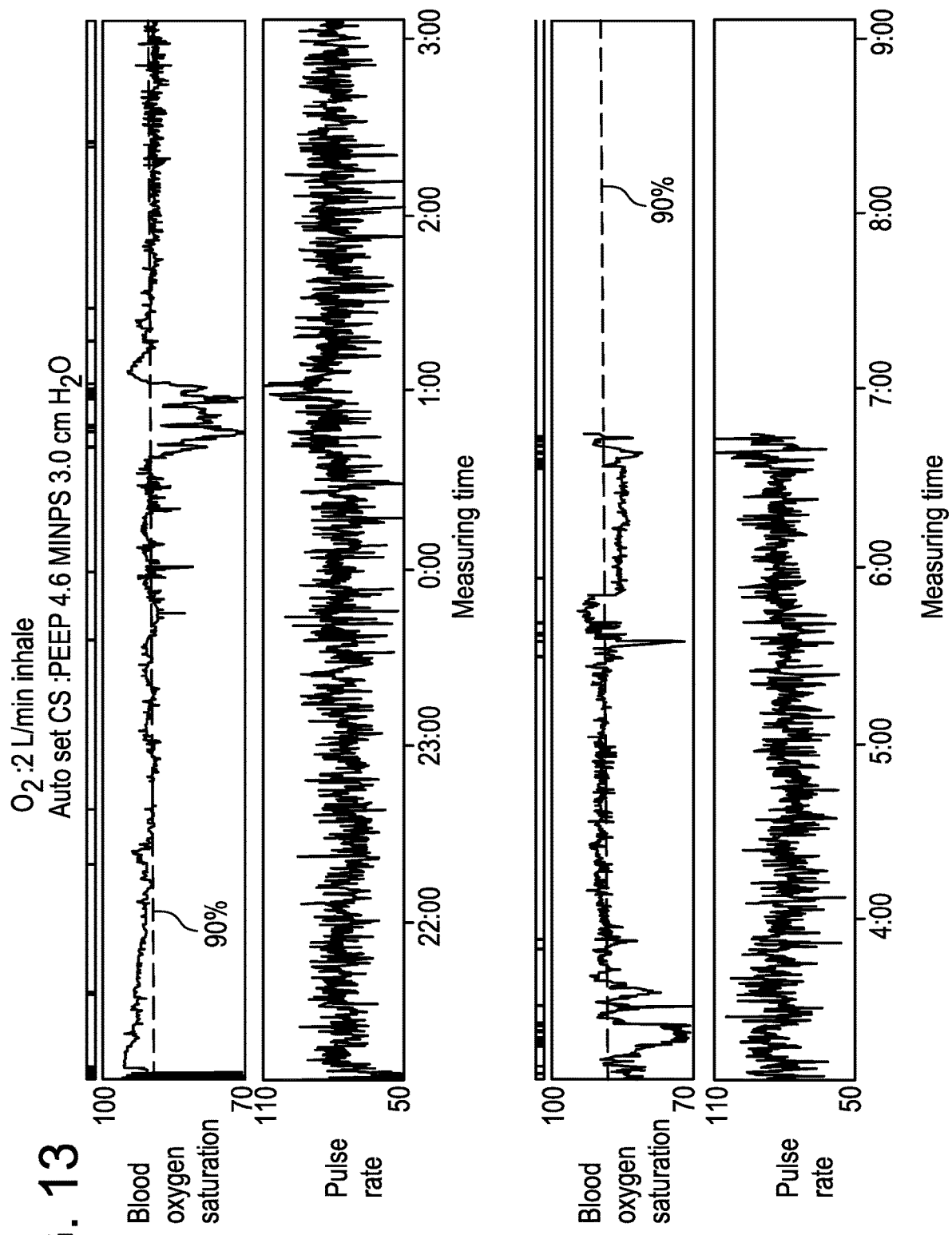
FIG. 13 is a diagram showing the SpO2 and the pulse rate of a CHF patient, in which PEEP is optimized by the congestive heart failure therapy device in Example 2.

FIG. 12 and FIG. 13 show an example in which oxygen administration and treatment with the congestive heart failure therapy device are combined, and adjusting PEEP within an optimum range achieves improvement of the condition.

In FIG. 12 in which PEEP is supplied by keeping an initial value at 4.0 cmH$_2$O, reduction of the baseline of SpO2 is observed throughout the night after 00:00, and it cannot be said that the effect of the congestive heart failure therapy device is obtained sufficiently.

FIG. 13 shows the result of adjusting PEEP of the congestive heart failure therapy device to increase PEEP to 4.6 cmH$_2$O. It is understood that reduction of the baseline of SpO2 caused by CHF disappears almost through the night, the pulse rate is suppressed to about 80, and the treatment effect is improved. In FIG. 13, the amount of oxygen administration is increased from 1 liter/minute to 2 liter/minute, compared with FIG. 12. The increase, however, is not such an amount that contributes to a rise of FiO2 (oxygen concentration in inhaled gas), considering the diffusion of administered oxygen by the flow of positive pressure air, and the oxygenation effect on improvement of the baseline of SpO2 is thought to be limited. The possibility of the diffusion of oxygen by the flow of positive pressure air is estimated also from the comparison between FIG. 11 and FIG. 12. More specifically, although the amount of oxygen administration is increased from 0.5 liter/minute to 1 liter/minute in FIG. 12, the baseline of SpO2 is reduced on the contrary, by the use of the congestive heart failure therapy device (positive pressure ventilation device) in combination. Therefore, the treatment effect in FIG. 13 is thought to be obtained by increasing PEEP of the congestive heart failure therapy device to 4.6 cmH$_2$O.

INDUSTRIAL APPLICABILITY

The congestive heart failure therapy device of the present invention is utilized, for example, in medical equipment manufacturing industry.

REFERENCE SIGNS LIST

1 Main body
2 Pressure raising unit
3 Control unit
4 Pulse oximeter
5 Mask
6 Input Unit
7 Output unit
8 Sensor
9 Blood flow meter
41 Pulse rate sensor

The invention claimed is:

1. A positive pressure therapy device for congestive heart failure patients, the positive pressure therapy device comprising:
   a pressure raising unit which is connected to a tube and configured to raise a pressure of an air or a gas mixture of the air and other gases to a positive pressure;
   a mask configured to be connected via the tube to the pressure raising unit and introduce the air or the gas mixture that is set to the positive pressure that is supplied from the pressure raising unit into an airway of a patient;
   a pulse oximeter configured to measure a blood oxygen level of the patient; and
   a processor configured to perform an automatic adjustment of a positive end expiratory pressure (PEEP) value P1 based on a value of the blood oxygen level that is measured by the pulse oximeter,
   wherein the positive pressure therapy device is configured to supply the air or the gas mixture so that the positive pressure is periodically varied between the PEEP value P1 and an air pressure value P2 in synchronization with a breath of the patient, wherein the air pressure value P2 is greater than the PEEP value P1, and wherein, in the automatic adjustment of the PEEP value P1, the processor is further configured to:
control the pressure raising unit to increase the PEEP value P1 of the patient based on the value of the blood oxygen level of the patient,
after the increasing the PEEP value P1, determine whether the increased PEEP value P1 has raised the value of the blood oxygen level,
based on the determining that the increased PEEP value P1 has raised the value of the blood oxygen level, increase the PEEP value P1 again,
based on the determining that the increased PEEP value P1 has not raised the value of the blood oxygen level, control the pressure raising unit to reduce the PEEP value P1 and determine whether the decreased PEEP value P1 has raised the value of the blood oxygen level, and
based on the determining that the decreased PEEP value P1 has not raised the value of the blood oxygen level, terminate the automatic adjustment of the PEEP value P1.

2. The positive pressure therapy device according to claim 1, wherein the processor is further configured to control the pressure raising unit to increase or reduce the PEEP value P1 based on the value of the blood oxygen level becoming equal to or smaller than a preset value of the blood oxygen level.

3. The positive pressure therapy device according to claim 2, wherein the processor is further configured to control the pressure raising unit to increase or reduce the PEEP value P1 by one level of a predetermined plurality of levels.

4. The positive pressure therapy device according to claim 1, wherein the value of the blood oxygen level is a value of a percutaneous oxygen saturation (SpO2).

5. The positive pressure therapy device according to claim 1, further comprising a pulse rate sensor configured to measure a pulse rate of the patient,
wherein the processor controls the pressure raising unit further based on the pulse rate measured by the pulse rate sensor.

6. The positive pressure therapy device according to claim 1, further comprising a sensor configured to measure the breath of the patient,
wherein the processor controls the pressure raising unit further based on a respiratory rate measured by the sensor.

7. A positive pressure therapy device for congestive heart failure patients, the positive pressure therapy device comprising:
a pressure raising unit configured to raise a pressure of an air or a gas mixture of the air and other gases to a positive pressure;
a mask configured to be connected to the pressure raising unit and introduce the air or the gas mixture that is set to the positive pressure that is supplied from the pressure raising unit into an airway of a patient;
a blood flow meter configured to measure a blood flow rate of the patient; and
a control unit comprising a processor and configured to perform an automatic adjustment of a positive end expiratory pressure (PEEP) value P1 based on a value of the blood flow rate that is measured by the blood flow meter, wherein the positive pressure therapy device is configured to supply the air or the gas mixture so that the positive pressure is periodically varied between the PEEP value P1 and an air pressure value P2 in synchronization with a breath of the patient, wherein the air pressure value P2 is greater than the PEEP value P1, and wherein, in the automatic adjustment of the PEEP value P1, the control unit is further configured to:
control the pressure raising unit to increase the PEEP value P1 of the patient based on the value of the blood flow rate,
after the increasing the PEEP value P1, determine whether the increased PEEP value P1 has raised the value of the blood flow rate,
based on the determining that the increased PEEP value P1 has raised the value of the blood flow rate, increase the PEEP value P1 again,
based on the determining that the increased PEEP value P1 has not raised the value of the blood flow rate, control the pressure raising unit to reduce the PEEP value P1 and determine whether the decreased PEEP value P1 has raised the value of the blood flow rate, and
based on the determining that the decreased PEEP value P1 has not raised the value of the blood flow rate, terminate the automatic adjustment of the PEEP value P1.

8. The positive pressure therapy device according to claim 7, wherein the control unit controls the pressure raising unit to increase or reduce the PEEP value P1 based on the value of the blood flow rate becoming equal to or smaller than a preset value of the blood flow rate.

9. The positive pressure therapy device according to claim 7, further comprising an invasive blood flow meter configured to measure a cardiac output of the patient by thermodilution,
wherein the control unit is further configured to perform the automatic adjustment of the PEEP value P1 further based on a value of the cardiac output.

10. A positive pressure value computing device for use in a positive pressure therapy for a patient with congestive heart failure, the positive pressure value computing device comprising:
a processor;
an input unit coupled to the processor and configured to acquire an input value comprising at least one of a value of a blood oxygen level, a value of a blood flow rate, or a value of a cardiac output of the patient;
a positive pressure value computing unit coupled to the processor and configured to compute a positive pressure value of a gas mixture to be supplied to the patient based on the input value, wherein the gas mixture of the positive pressure value is supplied to the patient; and
a positive pressure value output unit configured to output the positive pressure value,
wherein the positive pressure value is periodically varied between a positive end expiratory pressure (PEEP) value P1 and an air pressure value P2 in synchronization with a breath of the patient, wherein the air pressure value P2 is greater than the PEEP value P1, and
wherein the processor is further configured to perform an automatic adjustment of the PEEP value P1,
wherein, in the automatic adjustment, the processor is further configured to:

increase the PEEP value P1 based on the at least one of the value of the blood oxygen level, the value of the blood flow rate, or the value of the cardiac output, after the increasing the PEEP value P1, determine whether the increased PEEP value P1 has raised the at least one of the value of the blood oxygen level, the value of the blood flow rate, or the value of the cardiac output, based on the determining that the increased PEEP value P1 has raised the at least one of the value of the blood oxygen level, the value of the blood flow rate, or the value of the cardiac output, increase the PEEP value P1 again, based on the determining that the increased PEEP value P1 has not raised the at least one of the value of the blood oxygen level, the value of the blood flow rate, or the value of the cardiac output, reduce the PEEP value P1 and determine whether the decreased PEEP value P1 has raised the at least one of the value of the blood oxygen level, the value of the blood flow rate, or the value of the cardiac output, and based on the determining that the decreased PEEP value P1 has not raised the at least one of the value of the blood oxygen level, the value of the blood flow rate, or the value of the cardiac output, terminate the automatic adjustment of the PEEP value P1.

11. The positive pressure value computing device according to claim 10, wherein the input value is the value of the blood oxygen level of the patient.

12. The positive pressure value computing device according to claim 11, wherein the positive pressure value computing unit performs computations such that the PEEP value P1 to be supplied is increased or reduced based on the value of the blood oxygen level becoming equal to or smaller than a preset value of the blood oxygen level.

13. The positive pressure value computing device according to claim 12, wherein the positive pressure value computing unit performs computations such that the positive pressure value is increased or reduced by one level of a predetermined plurality of levels.

14. The positive pressure value computing device according to claim 11, wherein the value of the blood oxygen level is a value of the percutaneous oxygen saturation (SpO2).

15. The positive pressure value computing device according to claim 10, wherein the input value is the value of the blood flow rate or the value of the cardiac output.

16. The positive pressure value computing device according to claim 15, wherein the positive pressure value computing unit performs computations such that the PEEP value P1 to be applied is increased or reduced based on the value of the blood flow rate or the value of the cardiac output becoming equal to or smaller than a preset value of the blood flow rate or a preset value of the cardiac output.

17. The positive pressure value computing device according to claim 10, further comprising a pulse rate input unit for the patient, wherein the positive pressure value computing unit computes the positive pressure value further based on a value of a pulse rate of the patient obtained by the pulse rate input unit.

18. The positive pressure value computing device according to claim 10, further comprising a respiratory rate input unit coupled to the processor and configured to acquire a value of a respiratory rate of the patient, wherein the positive pressure value computing unit computes the positive pressure value further based on the value of the respiratory rate.

* * * * *